United States Patent [19]

Von Der Saal et al.

[11] Patent Number: 5,795,892

[45] Date of Patent: Aug. 18, 1998

[54] 4-AMINOPYRIDAZINES, METHOD OF PREPARING THEM AND DRUGS CONTAINING THESE COMPOUNDS

[75] Inventors: Wolfgang Von Der Saal, Weinheim; Reinhard Heck, Eberbach; Ralf Kucznierz, Ilvesheim; Herbert Leinert; Karlheinz Stegmeier, both of Heppenheim, all of Germany

[73] Assignee: Boehringer Mannheim GmbH, Mannheim, Germany

[21] Appl. No.: 793,445

[22] PCT Filed: Aug. 26, 1995

[86] PCT No.: PCT/EP95/03383

§ 371 Date: Feb. 28, 1997

§ 102(e) Date: Feb. 28, 1997

[87] PCT Pub. No.: WO96/06832

PCT Pub. Date: Mar. 7, 1996

[30] Foreign Application Priority Data

Aug. 30, 1994 [DE] Germany .................. 44 30 757.8

[51] Int. Cl.$^6$ .................. A61K 31/50; C07D 237/22; C07D 405/12; C07D 401/12
[52] U.S. Cl. .................. 514/247; 514/252; 544/238; 544/239; 544/240
[58] Field of Search .................. 544/238, 239, 544/240, 247, 252

[56] References Cited

FOREIGN PATENT DOCUMENTS 193853  9/1986  European Pat. Off. .

OTHER PUBLICATIONS

Shuman et al, *J. Med. Chem.* 36 p. 314–319 (1993).

*Primary Examiner*—Emily Bernhardt
*Attorney, Agent, or Firm*—Nikaido Marmelstein Murray & Oram LLP

[57] ABSTRACT

The invention concerns new 4-aminopyridazines of the general formula I

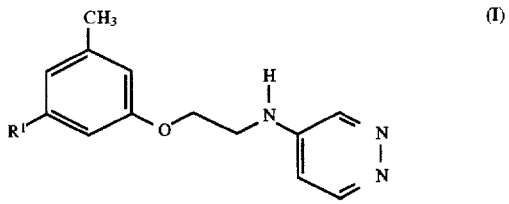

in which $R^1$ denotes an $R^2$—$SO_2$—O— or $R^2$—$SO_2$—$NR^3$— group in which $R^2$ denotes a cycloalkyl residue, an unsubstituted or substituted aryl or heteroaryl residue, $R^3$ denotes a hydrogen atom, an alkyl or alkyloxyalkyl group which can be unsubstituted or substituted once or several times by hydroxy groups wherein the hydroxy groups can be substituted by alkyl, hydroxyalkyl, alkyloxyalkyl, hydroxyalkyloxyalkyl or alkylcarbonyl groups and wherein in each case two vicinal hydroxy groups can be linked together by alkylidene groups, as well as hydrates, solvates and physiologically tolerated salts thereof. The invention also concerns the optically active forms, racemates and mixtures of diastereomers of these compounds, processes for their production and pharmaceutical agents containing these compounds having a thrombin-inhibiting action.

14 Claims, No Drawings

4-AMINOPYRIDAZINES, METHOD OF PREPARING THEM AND DRUGS CONTAINING THESE COMPOUNDS

The invention concerns new 4-aminopyridazines of the general formula I

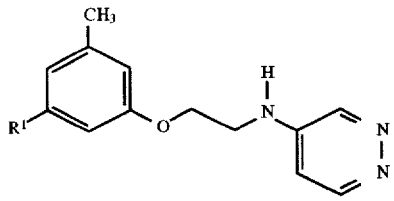

in which

R$^1$ denotes a R$^2$—SO$_2$—O— or R$^2$—SO$_2$—NR$^3$— group in which

R$^2$ denotes a cycloalkyl, an aryl or heteroaryl group in which the aryl or heteroaryl residues can be substituted once or several times by nitro, halogen, nitrile, hydroxy, carboxy, alkoxycarbonyl, phenylalkoxycarbonyl, phenyl, alkyl, trifluoromethyl, alkoxy, alkenyloxy, alkinyloxy, aralkyloxy, alkylthio, alkylsulfinyl, alkylsulfonyl, amino, alkylamino, dialkylamino, aralkylamino, diaralkylamino, alkylsulfonylamino, alkylcarbonylamino, formylamino, carbamoyl, thiocarbamoyl, alkylaminocarbonyl, dialkylaminocarbonyl or alkoxycarbonylalkyloxy, R$^3$ denotes a hydrogen atom, an alkyl or alkyloxyalkyl group which can be substituted once or several times by hydroxy groups wherein the hydroxy groups can be substituted by alkyl, hydroxyalkyl, alkyloxyalkyl, hydroxyalkyloxyalkyl or alkylcarbonyl groups and wherein in each case two vicinal hydroxy groups can be linked together by alkylidene groups, as well as hydrates, solvates and physiologically tolerated salts thereof. The invention also concerns a optically active forms, racemates and mixtures of diastereomers of these compounds.

The invention also concerns processes for the production of the above-mentioned compounds, pharmaceutical agents that contain such compounds as well as the use of these compounds in the production of pharmaceutical agents.

The aminopyridazines of the general formula I, their solvates and their salts inhibit the thrombin-induced coagulation of fibrinogen in blood as well as thrombin-induced aggregation of blood platelets. Thus they prevent formation of hyaline thrombi and platalet-rich thrombi and can be used to combat and prevent diseases such as thrombosis apoplexy, coronary infarction, inflammations and arteriosclerosis. Furthermore these compounds have an effect on tumour cells and prevent formation of metastases. As a result they can be used as anti-tumour agents.

Thrombin, the last enzyme of the coagulation cascade, cleaves fibrinogen to form fibrin which is cross-linked by factor XIIIa and becomes an insoluble gel which forms the matrix for a thrombus. Thrombin activates platelet aggregation by proteolysis of its receptor on the blood platelets and in this way also contributes to thrombus formation. When a blood vessel is damaged these processes are necessary in order to stop bleeding. No measurable thrombin concentrations are present in blood plasma under normal conditions. Increases in the thrombin concentration can lead to the formation of thrombi and hence to thromboembolic diseases which occur very frequently above all in industrial countries.

Thrombin is kept ready in plasma in the form of prothrombin and is released from it by factor Xa. Thrombin activates the factors V, VIII and XI by which means factor X is then converted into factor Xa. By this means thrombin catalyzes its own release which is why very rapid increases in thrombin concentrations can occur.

Thrombin inhibitors can therefore inhibit the release of thrombin, the platelet-induced and plasmatic blood coagulation.

There is a whole series of serine proteases apart from thrombin that cleave peptide substrates next to a basic amino acid. In order to limit side-effects, the thrombin inhibitors should be selective i.e. they should inhibit other serine proteases only slightly or not at all. Trypsin in particular being the least specific serine protease, can be easily inhibited by the various inhibitors. Trypsin inhibition can lead to pancreatic stimulation and to pancreatic hypertrophy (J. D. Geratz, Am. J. Physiol. 216, (1969) p. 812).

Plasma contains the protein plasminogen which is converted into plasmin by activators. Plasmin is a proteolytic enzyme whose activity is similar to that of trypsin. It serves to dissolve thrombi by degrading fibrin. Inhibition of plasmin would thus have the opposite effect to that which one would like to achieve by inhibiting thrombin.

Synthetic thrombin inhibitors have already been known for a long time. Substances of the (D)-Phe-Pro-Arg type were synthesized based on fibrinogen the natural substrate of thrombin. Such tripeptides imitate the amino acid sequence before the cleavage site on fibrinogen. In order to obtain good inhibitors the carboxylate group of the arginine was changed in such a way that the hydroxy group of serine 195 in the active site of thrombin can react with it. This can for example be achieved by replacing the carboxylate group by an aldehyde group. Corresponding (D)-Phe-Pro-arginals are described in the Patent Application EP-A 185390.

Benzamidine, a known trypsin inhibitor, was used as the basis for a second type of thrombin inhibitors. The inhibitors obtained in this way do not only differ from the (D)-Phe-Pro-Arg types in their chemical structure but also in the way they inhibit: serine 195 of thrombin does not bind to these inhibitors. This clearly follows from X-ray examinations of the structure (W. Bode, D. Turk, J. Stürzebecher, Eur. J. Biochem. 193, 175–182 (1990)). Nα-(2-naphthylsulfonylglycyl)-4-amidino-(R,S)-phenylalanine-piperidide ("NAPAP", DD 235866) belongs to this second class of thrombin inhibitors.

It was now surprisingly found that compounds of the general formula I which have no structures in common with the known thrombin inhibitors are selective thrombin inhibitors.

If R$^2$ in the compounds of the general formula I denotes a cycloalkyl group then this is understood as a ring with three to seven carbon atoms. If R$^2$ is an aryl group then this is understood as a phenyl and naphthyl group. A heteroaryl residue is understood for R$^2$ as monocyclic, bicyclic and tricyclic aromatics with heteroatoms such as nitrogen, oxygen or sulphur preferably furan, thiophene, pyrrole, oxazole, isoxazole, thiazole, isothiazole, imidazole, pyrazole, triazole, tetrazole, pyridine, pyrazine, pyrimidine, pyridazine, triazine, tetrazine, benzothiophene, dibenzothiophene, benzimidazole, carbazole, benzofuran, benzofurazan, benzo-2,1,3-thiadiazole, quinoline, isoquinoline, quinazoline.

Halogens as substituents of aryl or heteroaryl residues denote chlorine, bromine and iodine atoms, but preferably fluorine atoms.

Alkoxycarbonyl groups as substituents of the aryl or heteroaryl residues contain straight-chain or branched alkyl chains with 1 to 6 carbon atoms. Methoxycarbonyl and ethoxycarbonyl groups are preferred.

Aralkoxycarbonyl groups as substituents of aryl or heteroaryl residues contain a phenyl group linked to a $C_1$–$C_6$ alkyl chain. In this case a benzyloxycarbonyl group is preferred.

Alkyl groups as substituents of aryl or heteroaryl residues are straight-chain or branched and contain 1 to 6 carbon atoms. A methyl, ethyl, propyl, butyl, pentyl and hexyl group are preferred.

Alkoxy groups as substituents of aryl or heteroaryl residues contain 1 to 6 carbon atoms and are straight-chain or branched. A methoxy, ethoxy, n-propyloxy, i-propyloxy, n-butyloxy, i-butyloxy, tert.-butyloxy, pentyloxy and a hexyloxy group are preferred.

If $R^2$ in the general formula I denotes an aryl or heteroaryl group substituted by an alkenyloxy residue then this is understood as straight-chain or branched residues with 3 to 6 carbon atoms preferably an allyloxy group.

If $R^2$ in the general formula I denotes an aryl or heteroaryl group substituted by an alkinyloxy residue then this is understood as residues with 1 to 6 carbon atoms preferably a propargyloxy group.

If $R^2$ in the general formula I denotes an aryl or heteroaryl group substituted by an aralkyloxy residue then this is preferably a benzyloxy residue.

If $R^2$ in the general formula I denotes an aryl or heteroaryl group substituted by an alkylthio, alkylsulfinyl or alkylsulfonyl residue then this is understood as straight-chain or branched residues with 1 to 6 carbon atoms preferably a methylthio, methylsulfinyl or a methylsulfonyl group.

If $R^2$ in the general formula I denotes an aryl or heteroaryl group substituted by an alkylamino or dialkylamino residue then this is understood as straight-chain or branched residues with 1 to 6 carbon atoms preferably a methlyamino, dimethylamino and diethylamino group.

If $R^2$ in the general formula I denotes an aralkylamino residue or a di-aralkylamino residue then a benzylamino group and a bis(benzyl)amino group are particularly preferred.

If $R^2$ in the general formula I denotes an aryl or heteroaryl group substituted by an alkylsulfonylamino residue then this is understood as straight-chain or branched residues with 1 to 6 carbon atoms preferably a methlysulfonylamino group.

If $R^2$ in the general formula I denotes an aryl or heteroaryl group substituted by an alkylcarbonylamino residue then this is understood as straight-chain or branched residues with 1 to 6 carbon atoms preferably an acetylamino group.

If $R^2$ in the general formula I denotes an aryl or heteroaryl group substituted by an alkylaminocarbonyl or dialkylaminocarbonyl residue then this is understood as straight-chain or branched residues with 1 to 6 carbon atoms preferably a methylaminocarbonyl, dimethylaminocarbonyl or diethylaminocarbonyl group.

If $R^2$ in the general formula I denotes an aryl or heteroaryl group substituted by an alkoxycarbonylalkyloxy residue then an ethoxycarbonylmethyloxy group is especially preferred.

If $R^3$ in the general formula I is an alkyl group this is understood as straight-chain or branched alkyl chains with 1 to 6 carbon atoms. A methyl, ethyl, propyl, butyl, pentyl and hexyl group are preferred.

If $R^3$ in the general formula I denotes an alkyloxyalkyl group the alkyl residues are understood as straight-chain or branched alkyl chains with 1 to 6 carbon atoms. A methyloxyethyl, ethoxyethyl, propyloxyethyl and butyloxyethyl group are preferred.

If $R^3$ in the general formula I denotes an alkyl group substituted by one or several hydroxy groups this is understood as straight-chain or branched alkyl chains with 1 to 5 carbon atoms and 1 to 4 hydroxy groups. A 2-hydroxyethyl, 2,3-dihydroxypropyl and 2,3,4,5-tetra-hydroxypentyl group are preferred.

If $R^3$ in the general formula I denotes an alkyloxyalkyl group substituted by one or several hydroxy groups, the alkyls are straight or branched chains with 1 to 5 carbon atoms and carry 1 to 4 hydroxy groups. A 3-methoxy-2-hydroxy-propyl, 3-ethoxy-2-hydroxy-propyl, 3-(2-hydroxy-ethoxy) -2-hydroxy-propyl, 3-(3-hydroxy-propyloxy) -2-hydroxy-propyl, 3-(4-hydroxy-butoxy)-2-hydroxypropyl and a 3-(1,2-dihydroxy-ethoxy)-2-hydroxy-propyl group are preferred.

If the hydroxy groups mentioned as substituents for the alkyl and alkoxyalkyl residues for $R^3$ in the general formula I are substituted by alkyl, alkyloxyalkyl or hydroxyalkyloxyalkyl groups then the term "alkyl" is understood as straight-chain or branched alkyl chains with 1 to 5 carbon atoms. An ethyl, 2-methoxy-ethyl, 2-ethoxy-ethyl and a 2-(2-methoxy-ethoxy)ethyl group are preferred as substituents for hydroxyl groups.

If the hydroxy groups mentioned as substituents for the alkyl and alkoxyalkyl residues for $R^3$ in the general formula I are substituted by alkylcarbonyl groups then these are understood as straight-chain or branched groups with 2 to 6 carbon atoms, preferably an acetyl, propanoyl, butanoyl and pivaloyl group.

If the hydroxy groups mentioned as substituents for the alkyl and alkoxyalkyl residues for $R^3$ in the general formula I are present several times and are linked to one another in the vicinal position by alkylidene groups then the alkylidene groups contain 3 to 6 carbon atoms. A 2-propylidene group is preferred.

$R^1$ is in particular an $R^2$—$SO_2$—O and $R^2$—$SO_2$—$NR^3$ group.

$R^2$ is in particular a phenyl group which is unsubstituted or substituted once or several times by halogen (such as fluorine or chlorine), $C_1$–$C_6$ alkoxy (such as methoxy), carboxy, benzyloxycarbonyl, $C_1$–$C_6$ alkoxycarbonyl-$C_1$–$C_6$-alkyloxy (such as ethoxycarbonyl-methoxy), phenyl, nitrile or thiocarbamoyl; a naphthyl, thienyl or pyridyl group.

$R^3$ is in particular a hydrogen atom, a $C_1$–$C_6$ alkyl group substituted by one or several hydroxy groups (such as a 2-hydroxyethyl group, a 2,3-dihydroxypropyl group or a 2,3,4,5-tetrahydroxypentyl group), a $C_1$–$C_6$-alkyloxy-$C_1$–$C_6$-alkyl group substituted by one or several hydroxy groups (such as a 3-ethoxy-2-hydroxypropyl group, a 3-(4-hydroxy-butoxy) -2-hydroxy-propyl group or a 3-(2,3-dihydroxy-propyloxy) -2-hydroxy-propyl group), a $C_1$–$C_6$ alkyl group substituted by one or several hydroxy groups the hydroxy groups of which are independently either unsubstituted or substituted at least once by $C_1$–$C_6$-alkyloxy-$C_1$–$C_6$-alkyl groups (such as a 3-(2-methoxy-ethoxy)-2-hydroxy-propyl group), a $C_1$–$C_6$-alkyloxy-$C_1$–$C_6$-alkyl group substituted by one or several hydroxy groups the hydroxy groups of which are independently either unsubstituted or substituted at least once by $C_1$–$C_6$-alkyloxy-$C_1$–$C_6$-alkyl groups (such as a 3-{2-[2-(2-methoxy-ethoxy)-ethoxy]-ethoxy}-2-hydroxypropyl group), a $C_1$–$C_6$ alkyl group substituted by one or several hydroxy groups the hydroxy groups of which are acylated (such as a 2,3-diacetoxypropyl group) or in which two vicinal hydroxy groups are linked to one another by an alkylidene group (such as an isopropylidene group).

Compounds of the general formula I are preferred

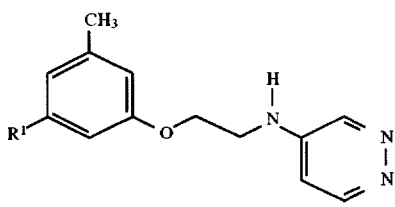

in which
R¹ denotes the group R²—SO₂—O— or R²—SO₂—NR³— in which
R² denotes a cyclohexyl, pyridinyl, thienyl, naphthyl or an unsubstituted phenyl group or a phenyl group substituted by one or several fluorine atoms, chlorine atoms, ethoxycarbonylmethyloxy, methoxy, benzyloxycarbonyl, phenyl, nitrile or thiocarbamoyl groups,
R³ denotes a hydrogen atom, a 2,3-dihydroxypropyl, 2,3-diacetoxy-propyl or a 2,2-dimethyl-[1,3]dioxolan-4-ylmethyl group.

The compounds of the general formula I are produced by well-known methods.

The amines of the general formula II are reacted with 3,4,5-trichloropyridazine to obtain a mixture of dichloropyridazines of the general formulae III and IV which are catalytically hydrogenated to form the compounds of the general formula I.

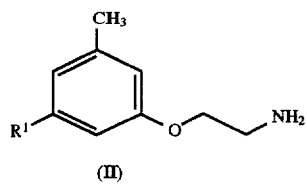

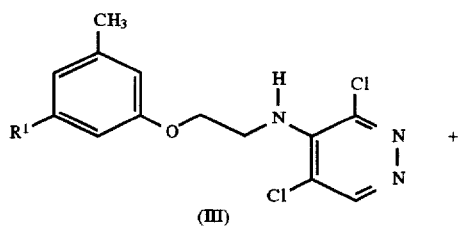

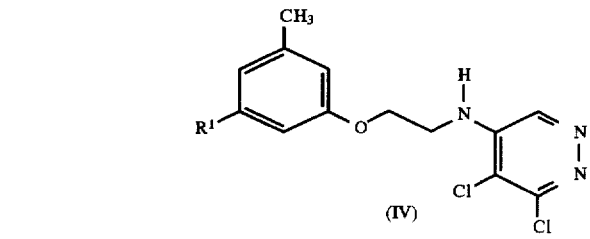

R¹ in the general formulae II, III and IV has the meanings stated above. The amines of the general formula II are reacted with 3,4,5-trichloropyridazine in an inert solvent such as toluene, tetrahydrofuran or dimethylformamide in the presence of one equivalent or a slight excess of an auxiliary base such as triethylamine, diisopropyl ethylamine or N-methyl-morpholine at temperatures between room temperature and 200° C., advantageously at the boiling point of the mixture. In this process the 4-alkylamino-3,4-dichloropyridazines of the general formula III and the 5-alkyl-amino-3,4-dichloropyridazines of the general formula IV are formed. These compounds can be separated for example by crystallisation or by column-chromatographic methods. However, a separation is not necessary because the desired compounds of the general formula I are generated from both compounds under the same conditions. The mixture of compounds of the general formulae III and IV that formed is therefore preferably reacted further. This mixture or the previously separated individual components are hydrogenated in an inert solvent such as methanol or ethanol in the presence of a catalyst such as palladium on carbon or Raney nickel and in the presence of a base such as N-methylmorpholine, triethylamine, potassium carbonate, sodium bicarbonate or sodium methylate. Hydrogenation can also be achieved in the absence of a base.

The compounds of the general formula II are obtained from compounds of the general formula V,

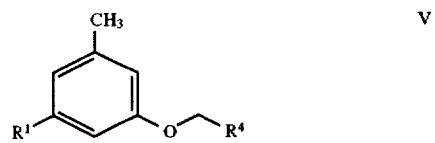

in which R¹ has the meanings given above and R⁴ is a nitrile group —CN, an amide group —CONH₂ or a phthalimido group. The aminomethyl group of the compounds of the general formula II is released from the residue R⁴ of the compounds of the general formula V in a well-known manner. In the case that R⁴ denotes a nitrile group this is achieved by hydrogenation in the presence of a catalyst such as Raney nickel or palladium on carbon or by reduction with lithium aluminium hydride or lithium borohydride in the presence of trimethylsilyl chloride. In the case that R⁴ denotes an amide group this is achieved by reduction with lithium aluminium hydride or lithium borohydride in the presence of trimethylsilyl chloride. In the case that R⁴ denotes a phthalimido group this is achieved by an acid such as hydrochloric acid or by a base such as sodium hydroxide solution or potassium hydroxide solution or by the action of hydrazine hydrate.

Compounds of the general formula V are produced from compounds of the general formula VI

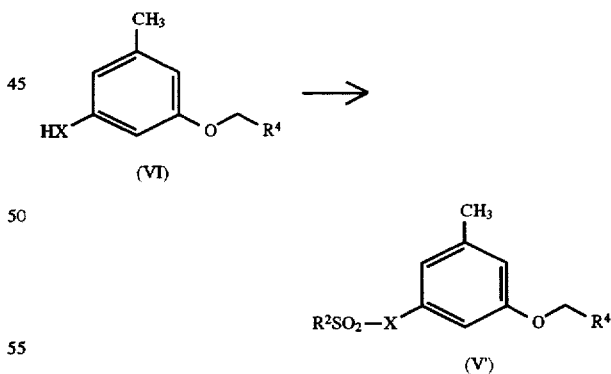

in which R⁴ has the above-mentioned meanings and X denotes an oxygen atom or an imino group —NH—. This is achieved by reaction with the sulfonic acid chlorides R²—SO₂Cl in which R² has the meanings given above. The sulfonic acid chlorides R²—SO₂Cl are commercially available or can be produced according to processes known from the literature ("Methoden der Organischen Chemie" (Houben-Weyl), Thieme Verlag, Stuttgart 1955p. 343: M. Quaedvlieg, "Aliphatische Sulfonsäuren"; p. 429: F. Muth, Aromatische Sulfonsäuren). In this process compounds of the general formula V' are firstly formed which represent that part of the compounds of the general formula V in which $R^1$ denotes the group $R^2$—$SO_2O$— and the group $R^2$—$SO_2$—NH—. The reaction is advantageously carried out with addition of an acid-binding agent such as e.g. alkali acetate, alkali hydroxide, calcium oxide, calcium carbonate, magnesium carbonate or with organic bases such as pyridine, triethylamine, N-methylmorpholine or di-isopropylethylamine, in which for example ether, methylene chloride, dioxane, toluene or an excess of the tertiary amine serve as the inert solvent. When using inorganic acid binders water, aqueous ethanol or aqueous dioxane are for example used as the reaction medium.

The remaining compounds of the general formula V namely the compounds of the general formula V'''

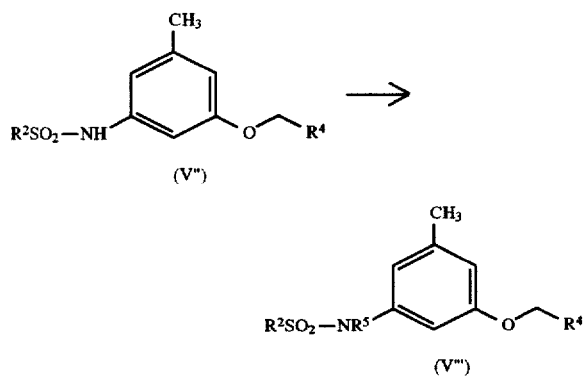

in which $R^5$ has the same meanings as $R^3$ with the exception of hydrogen, are produced from the compounds of the general formula V'' by alkylation. Compounds of the general formula $R^5$—Z are used as alkylating agents wherein $R^5$ has the same meaning as $R^3$ with the exception of the hydrogen atom and Z denotes a reactive group such as halogen, preferably bromine, chlorine or a sulfonate such as tosylate. These reactions are preferably carried out in a solvent such as acetone, ether, toluene or dimethylformamide at temperatures between $-30°$ C. and $100°$ C. preferably at room temperature in the presence of a base such as sodium hydride or calcium carbonate.

Compounds of the general formula VI are obtained from compounds of the general formula VII

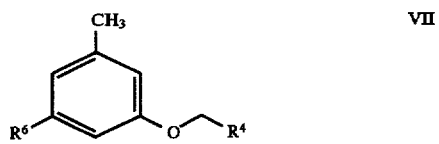   VII in which $R^4$ has the meanings given above and $R^6$ is a protected amino or hydroxy group. Protected amino groups are preferably understood as a benzyloxycarbonylamino group —NH—$CO_2CH_2Ph$, a tert.butyloxycarbonylamino group —NH—$CO_2$-t.Bu or a phthalimido group. A protected hydroxy group is preferably understood as arylsulfonyloxy groups preferably a phenylsulfonyloxy group. The amino group or hydroxy group is released in a well-known manner. The benzyloxycarbonylamino group is converted into a free amino group by hydrogenation in the presence of a catalyst such as Raney nickel or palladium on carbon or by an acid such as concentrated formic acid, hydrochloric acid or with hydrogen bromide in glacial acetic acid. The tert-.butyloxycarbonylamino group is converted into an amino group by an acid such as hydrochloric acid in dioxane, formic acid or trifluoroacetic acid. The phthalimido group is converted into an amino group by an acid such as hydrochloric acid or by a base such as sodium hydroxide solution or potassium hydroxide solution or by the action of hydrazine hydrate. Arylsulfonyloxy groups are converted into a free hydroxy group using lyes such as sodium hydroxide or potassium hydroxide.

Compounds of the general formula VII are produced by reacting phenols of the general formula VIII with compounds of the general formula IX.

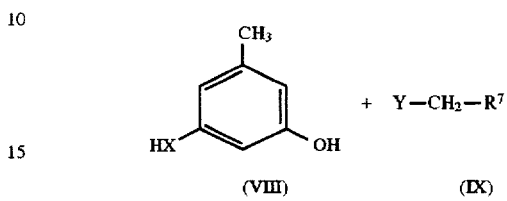

X in compounds of the general formula VIII has the above-mentioned meanings. In the compounds of the general formula IX $R^7$ has the same meanings as $R^4$ (a nitrile, amid or phthalimido group) and a carboxylic ester group. Y denotes a chlorine, bromine or iodine atom or a hydroxy or arylsulfonyloxy group. If Y is a chlorine, bromine or iodine atom or an arylsulfonyloxy group, the reaction preferably takes place in a solvent such as acetone, ether, toluene or dimethylformamide at temperatures between $-30°$ C. and $100°$ C., preferably in the presence of a base such as sodium hydride or potassium carbonate. If Y is a hydroxy group, the reaction is carried out in an inert solvent in the presence of diazodicarboxylic acid diethyl ester or diazodicarboxylic acid dipiperidide and triphenyl-phosphine. The compounds of the general formula VIII are commercially available (in the case that X denotes an oxygen atom) or known from the literature (F. Wessely, H. Eibel, G. Friedrich, "Monatshefte Chem."83, 24–30 (1952)). If $R^7$ is a carboxylic ester group then this is saponified preferably by potassium hydroxide in methanol and then converted into an amide group $CONH_2$ using ammonia. This conversion can also be carried out directly without prior saponification with the aid of $CH_3Al$ (Cl)$NH_2$ which is prepared from trimethylaluminium and ammonium chloride. Compounds of the general formula IX are commercially available.

Certain compounds of the general formula I can subsequently be converted into other compounds of the general formula I.

This concerns compounds of the general formula I in which $R^1$ denotes the group $R^2$—$SO_2$—O—. The residue $R^2$—$SO_2$— is cleaved off by the action of bases in an inert solvent preferably by potassium hydroxide in ethanol and firstly the intermediates of the general formula X are obtained

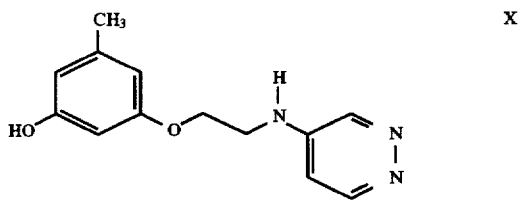   X which can be reacted with sulfonic acid chlorides $R^2SO_2Cl$ in which $R^2$ has the meanings given above. The reaction is advantageously carried out by adding an acid-binding agent such as for example alkali acetate, alkali hydroxide, calcium oxide, calcium carbonate, magnesium carbonate or with organic bases such as pyridine, triethylamine, N-methylmorpholine or di-isopropylmethylamine in which case for example ether, methylene chloride, dioxane, toluene or an excess of the tertiary amine serve as the inert solvent. Water, aqueous ethanol or aqueous dioxane are for example used as the reaction medium when inorganic acid binders are used.

This concerns compounds of the general formula I in which $R^2$ denotes an aryl or heteroaryl group which carry one or several benzyloxy or benzyloxycarbonyl groups as substituents. The benzyl group is in this case substituted by a hydrogen atom by catalytic hydrogenation in the presence of a catalyst preferably palladium on carbon. The benzyl group can also be removed by reaction with a strong acid such as trifluoroacetic acid in the presence of methylene, anisole or thioanisole.

This also concerns compounds of the general formula I in which $R^2$ denotes an aryl or heteroaryl group which carry one or several chlorine atoms as substituents. In this case the chlorine atom is substituted by a hydrogen atom by catalytic hydrogenation in the presence of a catalyst preferably palladium on carbon.

This also concerns compounds of the general formula I in which $R^2$ denotes an aryl or heteroaryl group which carry one or several nitro groups as substituents. In this case the nitro group is substituted by an amino group by catalytic hydrogenation in the presence of a catalyst preferably palladium on carbon.

This also concerns compounds of the general formula I in which $R^2$ denotes an aryl or heteroaryl group which carry one or several nitrile groups as substituents. These are converted into a thiocarbamoyl group by the action of hydrogen sulfide.

This also concerns compounds of the general formula I in which $R^1$ denotes a group $R^2SO_2NR^3$ in which $R^3$ is an alkyl or alkoxyalkyl group substituted by one or several hydroxy groups. The hydroxy groups are acylated by reaction with activated carboxylic acid derivatives preferably carboxylic acid chlorides such as e.g. acetyl chloride.

This also concerns compounds of the general formula I in which $R^1$ denotes the group $R^2SO_2NR^3$ in which $R^3$ is an alkyl or alkoxyalkyl group substituted by two vicinal hydroxy groups. Both vicinal hydroxy groups are linked by an alkylidene group by reaction with ketones for example by an isopropylidene group when using acetone.

Examples of salts of compounds of formula I which can be used physiologically are salts with physiologically tolerated mineral acids such as hydrochloric acid, sulphuric acid, sulphurous acid or phosphoric acid; or with organic acids such as methanesulfonic acid, p-toluenesulfonic acid, acetic acid, trifluoroacetic acid, citric acid, fumaric acid, maleic acid, tartaric acid, succinic acid or salicylic acid. The compounds of formula I with a free carboxy group can also form salts with physiologically tolerated bases. Examples of such salts are alkaline metal, alkaline-earth metal, ammonium and alkylammonium salts such as a sodium, potassium, calcium or tetramethylammonium salt.

The compounds of formula I can be solvated and in particular hydrated. The hydration can be achieved in the course of the production process or gradually occur as a result of hygroscopic properties of a compound of formula I which is firstly anhydrous.

Pure enantiomers of compounds of formula I can either be obtained by racemate resolution (by formation of salts with optically active acids or bases) or by using optically active starting materials in the synthesis.

For the production of pharmaceutical agents, the substances of the general formula I are mixed with suitable pharmaceutical carrier substances, aromatics, flavourings and dyes and are for example formed into tablets or dragees or are suspended or dissolved in water or oil e.g. olive oil with the addition of appropriate auxiliary substances.

The substances of the general formula I and their salts can be administered enterally or parenterally in a liquid or solid form. Water is preferably used as an injection medium which contains the usual additives in injection solutions such as stabilizers, solubilizers or buffers. Such additives are e.g. tartrate and citrate buffer, complexing agents (such as ethylenediaminetetra-acetic acid and their non-toxic salts) and high molecular polymers such as liquid polyethyleneoxide in order to regulate viscosity. Solid carrier materials are e.g. starch, lactose, mannitol, methylcellulose, talcum, highly dispersed silicic acids, high molecular fatty acids (such as stearic acid), animal and vegetable fats and solid high molecular polymers (such as polyethylene glycols). Preparations suitable for oral administration can, if desired, contain flavourings and sweeteners. The compounds are usually administered in amounts of 10–1500 mg per day in relation to 75 kg body weight. It is preferable to administer 1–2 tablets with a content of active substance of 5–500 mg. 2–3 times per day. The tablets can also be retarded as a result of which only 1–2 tablets have to be administered per day with 20–700 mg active substance. The active substance can also be administered by injection 1–8 times per day or by continuous infusion in which case 50–2000 mg per day are usually sufficient.

The following compounds are preferred within the sense of the invention in addition to those mentioned in the examples:

1. N-(2-Hydroxy-ethyl)-N-{3-methyl-5-[2-(pyridazin-4-ylamino)-ethoxy]-phenyl}-2-methoxy-benzenesulfonamide
2. N-(2,3,4,5-tetrahydroxy-pentyl)-N-{3-methyl-5-[2-pyridazin-4-ylamino)-ethoxy]-phenyl}-2-methoxy-benzenesulfonamide
3. N-(3-ethoxy-2-hydroxy-propyl)-N-{3-methyl-5-[2-(pyridazin-4-ylamino)-ethoxy]-phenyl}-2-methoxy-benzenesulfonamide
4. N-[2-Hydroxy-3-(4-hydroxy-butoxy)-propyl]-N-{3-methyl-5-[2-(pyridazin-4-ylamino)-ethoxy]-phenyl}-2-methoxy-benzenesulfonamide
5. N-[(1,2-Dihydroxy-ethoxy)-2-hydroxy-propyl]-N-{3-methyl-5-[2-(pyridazin-4-ylamino)-ethoxy]-phenyl}-2-methoxy-benzenesulfonamide
6. N-[2-Hydroxy-3-(2-methoxy-ethoxy)-propyl]-N-{3-methyl-5-[2-(pyridazin-4-ylamino)-ethoxy]-phenyl}-2-methoxy-benzenesulfonamide
7. N-{2-[2-(2-Methoxy-ethoxy)-ethoxy]-ethyl}-N-{3-methyl-5-[2-(pyridazin-4-ylamino)-ethoxy)]-phenyl}-2-methoxy-benzenesulfonamide
8. N-(2-Hydroxy-3-{2-[2-(2-methoxy-ethoxy)-ethoxy]-ethoxy}-propyl)-N-{3-methyl-5-[2-(pyridazin-4-ylamino)-ethoxy]-phenyl}-2-methoxy-benzenesulfonamide
9. N-(2,3-Dihydroxy-propyl)-N-{3-methyl-5-[2-(pyridazin-4-ylamino)-ethoxy]-phenyl}-2-ethoxy-benzenesulfonamide
10. N-(2,3-Dihydroxy-propyl)-N-{3-methyl-5-[2-(pyridazin-4-ylamino)-ethoxy]-phenyl}-2-propyloxy-benzenesulfonamide
11. N-(2,3-Dihydroxy-propyl)-N-{3-methyl-5-[2-(pyridazin-4-ylamino)-ethoxy]-phenyl}-2-(2-propyloxy)-benzenesulfonamide
12. N-(2,3-Dihydroxy-propyl)-N-{3-methyl-5-[2-(pyridazin-4-ylamino)-ethoxy]-phenyl}-2-butoxy-benzenesulfonamide 13. N-(2,3,4,5-tetrahydroxy-pentyl)-N-{3-methyl-5-[2-(pyridazin-4-ylamino)-ethoxy]-phenyl}-2-propyloxy-benzenesulfonamide
14. N-(2,3,4,5-tetrahydroxy-pentyl)-N-{3-methyl-5-[2-(pyridazin-4-ylamino)-ethoxy]-phenyl}-2-(2-propyloxy)-benzenesulfonamide
15. N-(2,3,4,5-tetrahydroxy-pentyl)-N-{3-methyl-5-[2-(pyridazin-4-ylamino)-ethoxy]-phenyl}-2-butoxy-benzenesulfonamide

EXAMPLE 1

N-{3-methyl-5-[2-(pyridazin-4-ylamino)-ethoxy]-phenyl}-benzenesulfonamide a) 96.0 g (0.78 mol) 3-hydroxy-5-methyl-aniline (F. Wessely, H. Eibel, G. Friedrich, "Monatshefte Chem." 83, 24–30, (1952)) in 1.2 l dioxane and 840 ml water was admixed with 420 ml 2N sodium hydroxide solution and with 171 g (0.78 mol) di-tert.butyl-dicarbonate while cooling on ice. It was stirred for 12 h at room temperature, the solvent was removed in a vacuum, it was acidified to pH=2–3 while cooling on ice and extracted with ethyl acetate. The organic phase was dried over sodium sulfate, filtered and the solvent was removed in a vacuum. 174 g (quantitative) N-(tert.butyloxy-carbonyl)-3-hydroxy-5-methyl-aniline was obtained as an oil. MS (m/e)=223.

b) 132 g (0.59 mol) of this compound in 400 ml dry dimethylformamide, 90 g (0.65 mol) potassium carbonate and 69 ml (0.65 mol) chloroacetic acid ethyl ester were heated for 3 h to 70° C. It was poured onto 1 l ice water, extracted with ethyl acetate, the organic phase was dried over sodium sulfate, it was filtered and the solvent was removed in a vacuum. 174 g (95%) 2-(3-tert.butyloxycarbonylamino -5-methyl-phenoxy)-acetic acid ethyl ester was obtained as an oil. MS (m/e)=309.

c) 174 g (0.562 mol) of this compound was admixed with 200 ml trifluoroacetic acid while cooling on ice, it was stirred for 2 h at room temperature and the solvent was removed in a vacuum. The residue was admixed with 2N hydrochloric acid, extracted with ethyl acetate, the aqueous phase was made alkaline with sodium hydroxide solution and extracted with ethyl acetate. The organic phase was dried with sodium sulfate, filtered and the solvent was removed in a vacuum. 87.5 g (74%) 2-(3-amino-5-methyl-phenyloxy)-acetic acid ethyl ester was obtained as an oil. MS (m/e)=209.

d) 74.8 g (0.357 mol) of this compound, 54.5 ml (0.357 mol) triethylamine and 50.3 ml (0.393 mol) benzenesulfonyl chloride in 300 ml dichloromethane were stirred for 1 h at room temperature. It was extracted with water, the organic phase was dried over sodium sulfate, filtered and the solvent was removed in a vacuum. 124 g (quant.) 2-(3-phenyl-sulfonylamino -5-methyl-phenyloxy)-acetic acid ethyl ester was obtained as an oil. MS (m/e)=349.

e) 124 g (357 mmol) of this compound and 60 g potassium hydroxide were stirred in 750 ml ethanol for 2 h at 70° C., the precipitate was filtered, dissolved in water, acidified with 6N hydrochloric acid, extracted with ethyl acetate, the organic phase was dried over sodium sulfate, filtered, the solvent was removed in a vacuum, the residue was digested with ether and 56 g (50%) 2-(3-phenyl-sulfonylamino -5-methyl-phenyloxy)-acetic acid of Fp 156°–159° C. was obtained.

f) 9.6 g (30 mmol) of this compound and 3.3 ml (30 mmol) N-methylmorpholine in 70 ml dichloromethane were cooled to −20° C. and 4.3 ml (33 mmol) isobutylchloroformate was added dropwise. The mixture was added dropwise into −20° C. cold methanolic ammonia solution and the precipitate was isolated. 8.7 g (91%) 2-(3-phenylsulfonylamino-5-methyl-phenyloxy)-acetamide of Fp 237°14 239° C. was obtained.

g) 8.6 g (27 mmol) of this compound and 3.1 g (81 mmol) lithium aluminium hydride were heated to boiling in 150 ml tetrahydrofuran for 2 h under reflux, water was added dropwise, it was filtered, the solvent was removed in a vacuum, the residue was taken up in ethyl acetate and extracted with water. The organic phase was dried over sodium sulfate, filtered and the solvent was removed in a vacuum. 7.0 g (84%) N-[3-(2-aminoethoxy)-5-methyl-phenyl]-benzenesulfonamide was obtained as an oil.
MS (m/e)=306.

h) 5.8 g (19 mmol) of this compound, 3.5 g (19 mmol) 3,4,5-trichloropyridazine and 22.6 ml (19 mmol) triethylamine in 70 ml tetrahydrofuran were stirred for 2 h at 120° C., the solvent was removed in a vacuum, water was added and it was extracted with ethyl acetate. The organic phase was dried over sodium sulfate, filtered and the solvent was removed in a vacuum. 2.4 g (28%) of a mixture of N-{3-[2-(3,5-dichloropyridazine-4-ylamino)-ethoxy]-5-methyl-phenyl}-benzenesulfonamide and N-{3-[2,3-dichloropyridazin -4-ylamino)-ethoxy]-5-methyl-phenyl }-benzenesulfonamide was obtained as an oil.
MS (m/e)=453.

i) 300 mg (0.7 mmol) of this compound was hydrogenated in 20 ml methanol in the presence of 100 mg Raney nickel for 16 h at normal pressure and room temperature. It was filtered, the solvent was removed in a vacuum, the residue was taken up in water, it was made alkaline with dilute sodium hydroxide solution, extracted with ethyl acetate, the organic phase was dried over sodium sulfate, filtered, the solvent was removed in a vacuum and 200 mg (79%) of the title compound was obtained as an amorphous mass. MS (m/e)=384.

EXAMPLE 2

Benzenesulfonic acid-3-methyl-5-[2-(pyridazin-4-ylamino)-ethoxy]-phenyl ester a) 24.8 g (200 mmol) 5-methyl-resorcinol, 200 ml ether, 400 ml sodium hydrogen carbonate solution and 28.2 ml (220 mmol) benzenesulfonyl chloride were stirred for 2 d at room temperature, the organic phase was separated, the aqueous phase was extracted with ether, the combined organic phases were dried over sodium sulfate, filtered, the solvent was removed in a vacuum and 52 g (quant.) benzenesulfonic acid-3-hydroxy-5-methyl-phenyl ester was obtained. Fp 108°–110° C.

b) 51.1 g (193 mmol) of this compound, 28.0 g (203 mmol) potassium carbonate and 12.7 ml (203 mmol) chloroacetonitrile in 220 ml dimethyl-formamide were stirred for 2 h at 70° C. Water was added, it was extracted with ethyl acetate, the organic phase was extracted with water, the organic phase was dried over sodium sulfate, filtered and the solvent was removed in a vacuum. 58 g (quant.) 3-benzenesulfonyloxy-5-methyl-phenyloxy-acetonitrile was obtained as an oil.

MS (m/e)=303.

c) 30 g (99 mmol) of this compound in 100 ml tetrahydrofuran was added dropwise to 10 g (460 mmol) lithium borohydride and 100 ml (790 mmol) chlorotrimethylsilane in 150 ml tetrahydrofuran. It was admixed with water, the solvent was removed in a vacuum, water was added to the residue and it was extracted with ethyl acetate. The organic phase was dried over sodium sulfate, filtered, the solvent was removed in a vacuum and 24.4 g (80%) benzenesulfonic acid-3-(2-amino-ethoxy)-5-methyl-phenyl ester was obtained as an oil. MS (m/e)=307.

d) This compound was reacted as described in example 1 h) and a mixture of benzenesulfonic acid-3-methyl-5-[2-(2,3-dichloropyridazin-4-ylamino)-ethoxy]-phenyl ester and benzenesulfonic acid-3-methyl-5-[2-(3,5-dichloropyridazin-4-ylamino)-ethoxy]-phenyl ester was obtained in a quantitative yield as an oil. MS (m/e)=454.

e) This compound was hydrogenated as described in example 1i) and the title compound of Fp 129°–132° C. was obtained in an 86% yield.

EXAMPLE 3

2-Chloro-benzenesulfonic acid-3-methyl-5-[2-(pyridazin-4-ylamino)-ethoxy]-phenyl ester a) 1.0 g (2.6 mmol) of the compound from example 2) and 0.15 g (13 mmol) potassium hydroxide in 5 ml ethanol were stirred for 2 d at room temperature, the solvent was removed in a vacuum, the residue was taken up in water, it was made neutral with 2N hydrochloric acid, extracted with ethyl acetate, the organic phase was dried over sodium sulfate, filtered, the solvent was removed in a vacuum and 0.3 g (47%) N-(4-pyridazinyl)-N-[2-(3-hydroxy-5-methyl-phenyloxy)-ethyl]-amine of Fp 193°14 195° C. was obtained.

b) 0.5 g (2 mmol) of this compound, 0.44 ml (4 mmol) N-methylmorpholine and 0.42 g (2 mmol) 2-chlorobenzenesulfonyl chloride in 5 ml tetrahydrofuran were stirred for 3 h at 60° C. The solvent was removed in a vacuum, the residue was taken up in water, extracted with dichloromethane, the organic phase was dried over sodium sulfate, filtered, the solvent was removed in a vacuum, the oily residue was filtered over silica gel and 190 mg (23%) of the title compound of Fp 138°–139° C. was obtained.

EXAMPLE 4

Pyridin-3-sulfonic acid-3-methyl-5-]-2-(pyridazin-4-ylamino)-ethoxy]-phenyl ester
was obtained in a 52% yield analogously to example 3) using pyridine-3-sulfonyl chloride in step 3b). Fp 131°–132° C.

EXAMPLE 5

Thiophene-2-sulfonic acid-3-methyl-5-[2-(pyridazin-4-ylamino)-ethoxy]-phenyl ester
was obtained in a 21% yield analogously to example 3) by using thiophene-2-sulfonyl chloride in step 3b). Fp 127° C.

EXAMPLE 6

3-Chlorobenzenesulfonic acid-3-methyl-5-[2-(pyridazin-4-ylamino)-ethoxy]-phenyl ester
was obtained in a 27% yield analogously to example 3) by using 3-chlorobenzenesulfonyl chloride in step 3b). Fp 137°–139° C.

EXAMPLE 7

2,3,5,6-Tetramethylbenzenesulfonic acid-3-methyl-5-[2-(pyridazin -4-ylamino)-ethoxy]-phenyl ester
was obtained in a 37% yield analogously to example 3) by using 2,3,5,6-tetramethylbenzenesulfonyl chloride in step 3b). Fp 113°–117° C.

EXAMPLE 8

2-{3-Methyl-5-[2-(pyridazin-4-ylamino)-ethoxy]-phenoxy sulfonyl}-benzoic acid 300 mg (1.2 mmol) of the compound from example 3a) and 220 mg (1.2 mmol) 2-sulfobenzoic acid anhydride were heated for 1 h to 210° C., the residue was separated by column chromatography (column: 25 cm long, diameter 4 cm; material: LiChrosphere RP 18 12 μm select B; mobile solvent: methanol/phosphate buffer pH=7.8 (40:60)). The solvent was removed from the appropriate fractions almost until dryness and 70 mg of the title compound of Fp>250° C. was obtained. MS (m/e)=429.

EXAMPLE 9

3-Cyanobenzenesulfonic acid-3-methyl-5-[2-(pyridazin-4-ylamino)-ethoxy]-phenyl ester
was obtained in a 17% yield analogously to example 3) by using 3-cyanobenzenesulfonyl chloride in step 3b). Fp 130°–133° C.

EXAMPLE 10

3-Thiocarbamoyl-benzenesulfonic acid-3-methyl-5-[2-(pyridazin-4-ylamino)-ethoxy]-phenyl ester Hydrogen sulfide was passed into a solution of 1.5 g (3.7 mmol) 3-cyanobenzenesulfonic acid-3-methyl-5-[2-(pyridazin-4-ylamino)-ethoxy]-phenyl ester (example 9) and 2.0 ml triethylamine in 20 ml pyridine until saturation (ca. 30 min). After 2 h at room temperature the solvent was removed in a vacuum, the residue was admixed with water, extracted with ethyl acetate, the solvent was removed in a vacuum, the residue was taken up in methanol and filtered over silica gel (dichloromethane: methanol=98:2). The solvent was removed in a vacuum and the title compound was obtained in a 87% yield as yellow crystals of Fp 76°–78° C.

EXAMPLE 11

4-Cyanobenzenesulfonic acid-3-methyl-5-[2-(pyridazin-4-ylamino)-ethoxy]-phenyl ester
was obtained in a 60% yield analogously to example 3) by using 4-cyanobenzenesulfonyl chloride in step 3b). Fp 180°–182° C.

EXAMPLE 12

4-Thiocarbamoyl-benzenesulfonic acid-3-methyl-5-[2-(pyridazin-4-ylamino)-ethoxy]-phenyl ester
was obtained in a 85% yield from the title compound of example 11 analogously to example 10. Fp 166°–186° C.

EXAMPLE 13

(3-{3-Methyl-5-[2-(pyridazin-4-ylamino)-ethoxy]-phenoxy-sulfonyl}-phenoxy)-acetic acid ethyl ester
was obtained in a 45% yield analogously to example 3) by using 3-ethoxycarbonylmethoxy-benzenesulfonyl chloride instead of 3-chlorobenzenesulfonyl chloride in step 3b). Oil. MS m/e=487.

EXAMPLE 14

2-{3-Methyl-5-[2-(pyridazin-4-ylamino)-ethoxy]-phenoxy-sulfonyl}-benzoic acid-benzyl ester
was obtained in a 21% yield analogously to example 3) by using 2-benzyloxy-carbonyl-benzenesulfonyl chloride in step 3b). Oil. MS m/e=519.

EXAMPLE 15

N-(2,3-Dihydroxypropyl)-N-{3-methyl-5-[2-(pyridazin-4-ylamino)-ethoxy]-phenyl}-2-methoxy-benzenesulfonamide a) 36.0 g (292 mmol) 3-amino-5-methylphenol and 73.5 g (496 mmol) phthalic acid anhydride were heated for 2 h to boiling under reflux in 280 ml glacial acetic acid. Water was added, it was heated for a short time, allowed to cool and filtered. 59.6 g (80%) 2-(3-hydroxy-5-methyl-phenyl)-isoindole-1,3-dione of Fp 174°–175° C. was obtained.

b) 59 g (233 mmol) 2-(3-hydroxy-5-methyl-phenyl)-isoindole-1,3-dione, 44 ml (700 mmol) chloroacetonitrile and 96.7 g (700 mmol) potassium carbonate were heated for 4 h to 80° C. in 300 ml dry dimethylformamide. It was poured onto 2 l water, filtered and 60.5 g (89%) [3-(1,3-dioxo-1,3-dihydro-isoindol-2-yl)-5-methyl-phenoxy]-acetonitrile of Fp 156°–157° C. was obtained.

c) 30.0 g (103 mmol) [3-(1,3-dioxo-1,3-dihydro-isoindol-2-yl)-5-methyl-phenoxy]-acetonitrile and 6.0 ml (123 mmol) hydrazine hydrate in 500 ml ethanol were stirred for 4 h at room temperature, the precipitate was suction filtered, digested with ether and 16.7 g (quant.) (3-amino-5-methyl-phenoxy)-acetonitrile of Fp 76°–77° C. was obtained.

d) 11.4 g (55 mmol) 2-methoxy-benzenesulfonyl chloride was added in portions at 10° C. to 8.9 g (55 mmol) (3-amino-5-methyl-phenoxy)-acetonitrile and 7.6 ml (55 mmol) triethylamine in 70 ml dichloromethane, it was stirred for 1 h at room temperature, extracted with water, the organic phase was dried over sodium sulfate, filtered, the solvent was removed in a vacuum, the residue was digested with ether and 8.5 g (46%) N-(3-cyanomethoxy-5-methyl-phenyl)-2-methoxy-benzene sulfonamide of Fp 156°–157° C. was obtained.

e) 18.8 ml (151 mmol) (2,2-dimethyl-[1,3]dioxolan-4-yl)-methanol and 28.6 g (150 mmol) toluene-4-sulfonyl chloride were stirred for 16 h at room temperature in 7 ml pyridine, it was poured onto 400 ml water, extracted twice with ethyl acetate, the combined ethyl acetate phases were washed with water, the organic phase was dried with sodium sulfate, filtered, the solvent was removed in a vacuum and 38.2 g (88%) toluene-4-sulfonic acid-(2,2-dimethyl-[1,3]dioxolan-4-ylmethyl)-ester was obtained as a colourless oil. MS (m/e)=286.

f) 3.0 g (125 mmol) sodium hydride and 30.5 g (105 mmol) toluene-4-sulfonic acid-(2,2-dimethyl-[1,3]dioxolan-4-ylmethyl)-ester was added to 31.5 g (95 mmol) N-(3-cyanomethoxy-5-methyl-phenyl)-2-methoxy -benzenesulfonamide in 100 ml dry dimethylformamide, it was heated for 3 d to 130° C., the solvent was removed in a vacuum, water was added to the residue, it was extracted with ethyl acetate, the organic phase was dried over sodium sulfate, filtered, the solvent was removed in a vacuum and the residue was filtered over 300 ml silica gel (ethyl acetate:isohexane=1:1). The solvent was removed in a vacuum and 31.4 g (74%) N-(3-cyanomethoxy-5-methyl-phenyl)-N-(2,2-dimethyl-[1,3]dioxolan]-4-ylmethyl)-2-methoxy-benzene-sulfonamide was obtained as an almost colourless oil. MS (m/e)=446.

g) 106 ml (840 mmol) chlorotrimethylsilane was added dropwise to 9.2 g (420 mmol) lithium borohydride in 300 ml dry tetrahydrofuran while cooling on ice, it was stirred for 1 h at room temperature, a solution of 31.4 g (70 mmol) N-(3-cyanomethoxy-5-methyl-phenyl)-N-(2,2-dimethyl-[1,3]dioxolan]-4-ylmethyl)-2-methoxy-benzenesulfonamide in 100 ml tetrahydrofuran was added dropwise, it was stirred for 1 h at room temperature, water was added and the solvent was removed in a vacuum. The residue was dissolved in water, extracted with ethyl acetate and the aqueous phase was evaporated to dryness. 27.1 g (95%) N-[3-(2-amino-ethoxy)-5-methyl-phenyl]-N-(2,3-dihydroxypropyl)-2-methoxy-benzene sulfonamide was obtained as a colourless oil. MS (m/e)=410.

h) 26.2 g (quant.) of a mixture of N-{3-[2-(3,5-dichloropyridazin-4-ylamino)-ethoxy]-5-methyl-phenyl}-N-(2,3-dihydroxypropyl)-2-methoxy-benzene-sulfonamide and N-{3-[2-(3,4-dichloropyridazin-5-ylamino)-ethoxy]-5-methyl-phenyl}-N-(2,3-dihydroxy-propyl)-2-methoxy-benzenesulfonamide was obtained as an oil from 19.4 g (47 mmol) N-[3-(2-amino-ethoxy)-5-methyl-phenyl]-N-(2,3-dihydroxy-propyl)-2-methoxy-benzenesulfonamide, 6.9 ml (51 mmol) triethylamine and 9.2 g (51 mmol) 3,4,5-trichloropyridazine in 300 ml dry tetrahydrofuran according to the instructions of example 1 h). MS (m/e) =557.

i) This mixture was hydrogenated in 500 ml methanol in the presence of 19.5 g (143 mmol) potassium carbonate and 2 g 10% palladium on carbon. It was filtered, the solvent was removed in a vacuum, the residue was filtered over silica gel (dichloromethane:methanolic ammonia=95:5), the solvent was removed in a vacuum and 8.1 g (35%) of the title compound was obtained as an amorphous mass.
MS (m/e) =488.

EXAMPLE 16

N-(2,3-Dihydroxypropyl)-N-{-3-methyl-5-[2-(pyridazin-4-ylamino)-ethoxy]-phenyl}-benzenesulfonamide
was obtained analogously to example 15 by using benzenesulfonyl chloride instead of 2-methoxybenzenesulfonyl chloride in step d). Yield 67%, amorphous.
MS m/e=458.

EXAMPLE 17

N-(2,3-Dihydroxypropyl)-N-{3-methyl-5[2-(pyridazin-4-ylamino)-ethoxy]-phenyl}-2-fluoro benzenesulfonamide
was obtained analogously to example 15 by using 2-fluoro-benzenesulfonyl chloride instead of 2-methoxy-benzenesulfonyl chloride in step d). Yield 80%, amorphous.
MS m/e=476.

EXAMPLE 18

N-(2,3-Dihydroxypropyl)-N-{3-methyl-5-[2-(pyridazin-4-ylamino) -ethoxy]-phenyl}-4-fluoro-2-methyl-benzenesulfonamide
was obtained analogously to example 15 by using 4-fluoro-2-methyl-benzenesulfonyl chloride instead of 2-methoxybenzenesulfonyl chloride in step d). Yield 71%, amorphous. MS m/e=490.

EXAMPLE 19

N-(2,3-Dihydroxypropyl)-N-{3-methyl-5-[2-(pyridazin-4-ylamino) -ethoxy]-biphenyl-2-sulfonamide was obtained analogously to example 15 by using biphenyl-2-sulfonyl chloride instead of 2-methoxy-benzene-sulfonyl chloride in step d). Yield 85%, amorphous. MS m/e=534.

EXAMPLE 20

N-{3-Methyl-5-[2-(pyridazin-4-ylamino)-ethoxy]-phenyl}-2-methoxy-benzenesulfonamide a) 24.9 g (75 mmol) N-(3-cyanomethoxy-5-methyl-phenyl)-2-methoxy-benzenesulfonamide (example 15d) and 8.3 g (220 mmol) lithium aluminium hydride were heated for 2 h to boiling under reflux in 250 ml dry tetrahydrofuran. Water was added, it was filtered, the solvent was removed in a vacuum, it was digested with water and 10.8 g (41%) N-[3-(2-aminoethoxy)-5-methyl-phenyl]-2-methoxy-benzene-sulfonamide of Fp 133°–135° C. was obtained.

b) 14.5 g (quant.) of a mixture of N-{3-[2-(3,5-dichloropyridazin-4-ylamino)-ethoxy]-5-methyl-phenyl}-benzenesulfonamide and N-{3-[2-(2,3-dichloropyridazin-4-ylamino)-ethoxy]-5-methyl-phenyl}-benzenesulfonamide was obtained therefrom as an oil analogously to example 1 h). MS (m/e)=483.

c) The title compound of Fp 212–214° C was obtained therefrom analogously to example 1i) in a 65% yield.

EXAMPLE 21

Acetic acid-2-acetoxy-3-((2-methoxybenzenesulfonyl)-{3-methyl-5-[2-(pyridazin-4-ylamino) )-ethoxy]-phenyl}-amino)-propel ester 1.0 g (2 mmol) N-(2,3-dihydroxypropyl)-N-{3-methyl-5-[2-(pyridazin-4-ylamino)-ethoxy]-phenyl}-2-methoxy-benzene-sulfonamide (example 15) and 0.92 ml (13 mmol) acetyl chloride in 10 ml glacial acetic acid were stirred for 60 h at room temperature, the solvent was removed in a vacuum, the residue was taken up in dichloromethane, extracted with aqueous bicarbonate solution, the organic phase was dried over sodium sulfate, filtered, the solvent was removed in a vacuum and 1.1 g (quant.) of the title compound was obtained as an oil.
MS (m/e)=572.

EXAMPLE 22

N-{3-Methyl-5-[2-(pyridazin-4-ylamino)-ethoxy]-phenyl}-cyclohexanesulfonamide was obtained in a 41% yield analogously to example 20. Amorphous. MS m/e=390. The starting material (N-(3-cyanomethoxy-5-methyl-phenyl)-cyclohexane sulfonamide was obtained analogously to example 15d) by using cyclohexane sulfonyl chloride instead of 2-methoxy-benzenesulfonyl chloride.

EXAMPLE 23

Naphthalene-1-sulfonic acid-(2,2-dimethyl-[1,3] dioxolan-4-ylmethyl)-{3-methyl-5-[2-(1pyridazin-4-ylamino)-ethoxy]-phenyl}-amide was obtained in a 32% yield analogously to example 15 by using 1-naphthalenesulfonyl chloride instead of 2-methoxybenzenesulfonyl chloride in step d). Amorphous MS m/e=548.

EXAMPLE 24

N-(2 3,4,5-Tetrahydroxy-pentyl)-N-{ 13-methyl-5-[2-(pyridazin-4-ylamino)-ethoxy]-phenyl}-2-methoxy-benzene sulfonamide a) Toluene-4-sulfonic acid-2,2,2',2'-tetramethyl-[4,4'|bi| |1,3|dioxolanly|-5-methyl-ester was produced in a 65% yield analogously to example 15e) from (2,2,2', 2'-tetramethyl-|4,4'|bi||1,3|-dioxolanyl|-5-yl)-methanol which was obtained from xylite and acetone, and toluenesulfonic acid chloride. Fp 74°–76° C.

b) N-(3-Cyanomethoxy-5-methyl-phenyl)-2-methoxy-N-(2,2,2',2'-tetramethyl-|4,4'|bi||1,3|dioxolanly|-5-ylmethyl)-benzenesulfonamide was produced analogously to example 15f in a 72% yield from toluene-4-sulfonic acid-2,2,2',2'-tetramethyl-|4,4'|bi||1,3| dioxolanyl|-5-methyl-ester and N-(3-cyanomethoxy-5-methyl-phenyl)-2-methoxy-benzenesulfonamide (example 15d). Fp 128°–132° C.

c) N-[3-(2-amino-ethoxy)-5-methyl-phenyl]-2-methoxy-N-(2,3,4,5-tetrahydroxy-pentyl)-benzenesulfonamide was produced by reduction analogously to example 15 g in a 36% yield from N-(3-cyanomethoxy-5-methyl-phenyl)-2-methoxy-N-(2,2,2',2'-tetramethyl-|4,4'|bi| |1,3|dioxolanyl|-5-ylmethyl)-benzene-sulfonamide . Oil. MS (m/e)=470.

d) A mixture of N-{3-[2-(3,5-dichloropyridazin-4-ylamino)-ethoxy]-5-methyl-phenyl}-2-methoxy-N(2, 2,2',2'-tetramethyl-|4,4]bi[[1,3]dioxolanyl]-5-ylmethyl) -benzenesulfonamide and N-{3-[2-(3,4-dichloro-pyridazin-5-ylamino)-ethoxy]-5-methyl-phenyl}-2-methoxy-N(2,2,2',2'-tetramethyl-[4,4]bi[[1, 3]dioxolanyl]-5-ylmethyl)benzene-sulfonamide was obtained analogously to example 15 h) in a 65% yield as an oil by reaction of N-[3-(2-amino-ethoxy)-5-methyl-phenyl]-2-methoxy-N-(2,3,4,5-tetrahydroxy-pentyl)-benzenesulfonamide with 3,4,5-trichloropyridazine. MS (m/e)=617.

e) The title compound was obtained therefrom as a colourless oil in a 30% yield by hydrogenation analogously to example 15i. MS (m/e)=549.

EXAMPLE 25

Description of pharmacological experiments
Thrombin time

A conventional test in clinical coagulation diagnostics is the thrombin time. This parameter measures the action of thrombin on fibrinogen and the formation of clots. Inhibitors of thrombin result in an extended thrombin time.

In order to obtain plasma 9 parts of fresh blood from healthy donors was mixed with one part of sodium citrate solution (0.11 mol/l) and it was centrifuged for 10 minutes at room temperature at ca. 3000 r.p.m. The plasma was removed by pipette and can be stored at room temperature for ca. 8 hours.

200 µl citrate plasma was incubated for 2 minutes at 37° C. in a ball coagulometer (KC10 from the Amelung Company). 10 µl dimethylsulfoxide (DMSO) or a solution of the active substance in DMSO was added to 190 µl pre-heated thrombin reagent (Boehringer Mannheim GmbH; contains ca. 3 U/ml horse thrombin and 0.0125M $Ca^{++}$). On addition of this 200 µl solution to the plasma a stopwatch was started and the time at which coagulation starts was determined. The thrombin time was ca. 24 sec. in control measurements and was substantially increased by the active substances.

The measured thrombin times in seconds are given in the following table as a difference to the control. The concentrations of the active substances in human plasma were 50 µM (TT50) and 5 µM (TT5).

Thrombin inhibition

The kinetic measurements were carried out in 0.1M phosphate buffer that contained 0.2M sodium chloride and 0.5% polyethylene glycol 6000 at a pH=7.5 and 25° C. with the substrate H-(D)-Phe-Pro-Arg-pNA (Kabi) and human α thrombin (Sigma, specific activity=2150 NIH-units/mg) in polystyrene semi-microcuvettes in a total volume of 1 ml.

In a preliminary test each active substance was determined as to whether it inhibits thrombin rapidly or slowly. For this the reaction was firstly started by adding 0.03 NIH units thrombin to a 100 µM solution of the substrate and the active substance. In a second experiment, substrate was added to a solution of thrombin and the active substance which had been incubated for 5 minutes. The increase in the concentration of p-nitroaniline with time was monitored spectroscopically (UV-VIS spectrophotometer Lambda-2 from the Perkin-Elmer Company) at 405 nm for 12 min.

Since the measured curves obtained in both experiments were linear and parallel, the active substances of the following table are rapid thrombin inhibitors.

The inhibition constants $K_i$ were then determined as follows. The substrate was used at concentrations of 100 µM, 50 µM, 30 µM, 20 µM and at each substrate concentration one measurement was carried out without inhibitor and three measurements were carried out in the presence of various concentrations of the inhibitors listed in the following table. The reactions were started by the addition of thrombin. The increase in absorbance at 405 nm due to the formation of p-nitroaniline was monitored over a time period of 12 minutes. Measurement points (time versus absorbance) were transferred to a PC at intervals of 20 seconds. The rates $V_o$ (change in absorbance per second; measurements without inhibitor) and $V_i$ (measurements with inhibitor) are determined by linear regression. Only that part of each measurement was used in which the substrate concentration had decreased by less than 15%. $K_m'$ and $V_{max}$ were determined from a measurement series (constant inhibitor concentration, variable substrate concentrations) by a non-linear fit to the equation $$V = \frac{V_{max}*[S]}{[S]+K_m'}$$

Finally $K_i$ was calculated from the entire series of measurements by non-linear fitting to the equation $$V = \frac{V_{max}*[S]}{K_m*(1+[S]/K_i)+[S]}$$

The Michaelis constant $K_m$ was 3.8±2 µM in all measurements.

The inhibition constants $K_i$ of the active substances are stated in the following table in units of µM.

Inhibition of trypsin and plasmin 10 mg bovine pancreatic trypsin (Sigma) was dissolved in 100 ml 1 mM hydrochloric acid and stored in a refrigerator. 20 µl of this was admixed with 980 µl 1 mM hydrochloric acid. 25 µl thereof was used for each measurement. The measurement was carried out as described for thrombin. $K_m$=45 µM.

The measurements with human plasmin (Sigma, 10 units) were carried out as described for thrombin using the substrate S-2251 (H-(D)-Val-Leu-Lys-pNA, Kabi). 0.01 units plasmin were used for each measurement. $K_m$=250 µM.

| Compound of example | TT50 | TT5 | $K_i$ [µM] thrombin |
|---|---|---|---|
| 1 | 126 | 23 | 0.07 |
| 4 | 194 | 38 | 0.06 |
| 9 | 128 | 31 | 0.14 |
| 10 | 71 | 13 | 0.17 |
| 11 | 81 | 18 | 0.20 |
| 13 | 49 | 0 | 0.09 |
| 22 | 90 | 11 | 0.35 |

A trypsin and plasmin inhibition was not found for the compounds according to the invention.

We claim:

1. Compound of the formula

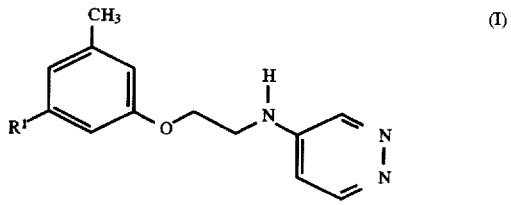

wherein
  $R^1$ is an $R^2$—$SO_2$—O— or $R^2$—$SO_2$—$NR^3$— group wherein
  $R^2$ is $C_3$–$C_7$ cycloalkyl or a member selected from the group consisting of phenyl, naphthyl, thiophenyl and pyridyl, wherein said member is unsubstituted or substituted at least once by nitro, halogen, nitrile, hydroxy, carboxy, $C_1$–$C_{16}$-alkoxycarbonyl, phenyl-$C_1$–$C_6$ alkoxycarbonyl, phenyl, $C_1$–$C_6$ alkyl, trifluoromethyl, $C_1$–$C_6$ alkoxy, $C_3$–$C_6$ alkenyloxy, $C_1$–$C_6$ alkinyloxy, benzyloxy, $C_1$–$C_6$ alkylthio, $C_1$–$C_6$ alkylsulfinyl, $C_1$–$C_6$ alkylsulfonyl, amino, $C_1$–$C_6$ alkylamino, di $C_1$–$C_6$ alkylamino, benzylamino, bis(benzyl)amino, $C_1$–$C_6$ alkylsulfonylamino, $C_1$–$C_6$ alkylcarbonylamino, formylamino, carbamoyl, thiocarbamoyl, $C_1$–$C_6$ alkylaminocarbonyl, di-$C_1$–$C_6$-alkylaminocarbonyl or $C_1$–$C_6$-alkoxycarbonyl-$C_1$–$C_6$-alkoxy, and
  $R^3$ is hydrogen, $C_1$–$C_6$ alkyl or $C_1$–$C_6$-alkyloxy-$C_1$–$C_6$-alkyl, wherein the alkyl or alkyloxyalkyl group is unsubstituted or substituted at least once by hydroxy which in turn is unsubstituted or substituted by $C_1$–$C_5$ alkyl, hydroxy $C_1$–$C_5$ alkyl, $C_1$–$C_5$ alkyloxy-$C_1$–$C_5$-alkyl, $C_1$–$C_5$ hydroxy alkyloxy-$C_1$–$C_5$-alkyl or $C_2$–$C_6$-alkylcarbonyl, and wherein in each case two vicinal hydroxyl groups are unlinked or are linked together by an $C_3$–$C_6$-alkylidene group,
  and optically active forms, racemates, diastereomer mixtures, hydrates, or physiologically tolerated salts thereof.

2. Compound of claim 1, wherein $R^1$ is $R^2$—$SO_2$—O—.

3. Compound of claim 1, wherein $R^1$ is $R^2$—$SO_2$—$NR^3$—.

4. Compound of claim 1, wherein the compound is N-{3-methyl-5-[2-(pyridazin-4-ylamino)-ethoxy]-phenyl}-benzenesulfonamide.

5. Compound of claim 1, wherein the compound is pyridin-3-sulfonic acid-3-methyl-5-[2-(pyridazin-4-ylamino)-ethoxy]-phenyl ester.

6. Compound of claim 1, wherein the compound is 3-cyanobenzenesulfonic acid-3-methyl-5-[2-(pyridazin-4-ylamino)-ethoxy]-phenyl ester.

7. Compound of claim 1, wherein the compound is 3-thiocarbamoylbenzenesulfonic acid-3-methyl-5-[2-(pyridazin-4-ylamino)-ethoxy]-phenyl ester.

8. Compound of claim 1, wherein the compound is 4-cyanobenzenesulfonic acid-3-methyl-5-[2-(pyridazin-4-ylamino)-ethoxy]-phenyl ester.

9. Compound of claim 1, wherein the compound is (3-{3-methyl-5-[2-(pyridazin4-ylamino)-ethoxy]-phenoxysulfonyl}-phenoxy)-acetic acid ethyl ester.

10. Compound of claim 1, wherein the compound is N-{3-methyl-5-[2(-pyridazin-4-ylamino)-ethoxy]-phenyl}-cyclohexanesulfonamide.

11. Compound of claim 1, wherein $R^2$ is a naphthyl, thienyl, pyridyl or phenyl residue which is unsubstituted or substituted at least once by halogen, $C_1-C_6$-alkoxy, carboxy, benzyloxycarbonyl, ethoxycarbonylmethyl, phenyl, nitrile, or thiocarbamoyl.

12. Compound of claim 1, wherein $R^3$ is hydrogen, $C_1-C_6$ alkyl substituted by at least one hydroxyl, $C_1-C_6$ alkyloxy-$C_1-C_6$ alkyl substituted by at least one hydroxyl group, $C_1-C_6$ alkyl substituted by at least one hydroxyl group wherein the hydroxyl group(s) are independently either unsubstituted or substituted at least once by $C_1-C_6$-alkoxy-$C_1-C_6$-alkyl, $C_1-C_6$-alkyloxy-$C_1-C_6$-alkyl substituted by at least one hydroxyl group wherein the hydroxyl group(s) are independently either unsubstituted or substituted at least once by $C_1-C_6$-alkyloxy-$C_1-C_6$-alkyl, or $C_1-C_6$alkyl substituted by at least one hydroxyl wherein the hydroxyl is acylated or $R^3$ is wherein two hydroxyl groups are linked to one another by an alkylidene group.

13. Pharmaceutical composition suitable for the treatment of thromboembolic diseases comprising a compound of claim 1 and a pharmaceutically acceptable carrier.

14. A method of treating a thromboembolic disease in a patient in need of such treatment, said method comprising administering to said patient an effective amount of a compound of claim 1.

* * * * *

UNITED STATES PATENT AND TRADEMARK OFFICE
CERTIFICATE OF CORRECTION

PATENT NO. : 5,795,892

DATED : August 18, 1998

INVENTOR(S) : Von Der Saal et al.

It is certified that error appears in the above-identified patent and that said Letters Patent is hereby corrected as shown below:

```
TITLE PAGE:
Item [73], line 1, delete "Manneim" insert therefor

-- Mannheim --
```

Signed and Sealed this

Twenty-fourth Day of November, 1998

Attest:

BRUCE LEHMAN

Attesting Officer

Commissioner of Patents and Trademarks